(12) United States Patent
Nishizuka et al.

(10) Patent No.: US 7,439,382 B2
(45) Date of Patent: Oct. 21, 2008

(54) 4-ALKYL-2-HALOANILINE DERIVATIVES AND PROCESS FOR PRODUCING THE SAME

(75) Inventors: Toshio Nishizuka, Tokyo-To (JP); Hiroshi Kurihara, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 476 days.

(21) Appl. No.: 10/508,161

(22) PCT Filed: May 16, 2003

(86) PCT No.: PCT/JP03/06157

§ 371 (c)(1),
(2), (4) Date: Sep. 17, 2004

(87) PCT Pub. No.: WO03/097572

PCT Pub. Date: Nov. 27, 2003

(65) Prior Publication Data

US 2005/0143454 A1    Jun. 30, 2005

(30) Foreign Application Priority Data

May 17, 2002    (JP)    ............................. 2002-142444

(51) Int. Cl.
*C07C 261/00*    (2006.01)
(52) U.S. Cl. ........................................................ 560/24
(58) Field of Classification Search ................... 560/24; 514/485
See application file for complete search history.

(56) References Cited

U.S. PATENT DOCUMENTS 4,436,936 A    3/1984    Howell

FOREIGN PATENT DOCUMENTS

WO    WO 01/92231    12/2001

OTHER PUBLICATIONS

Nebergall et al, College Chemistry With Qualitaitve Analysis, 6th Ed, 1980, p. 89, 3 Pages.*
Thornton, T.J., et al., *Metallation of N-(Pivaloyl)—and N-(tert-Butoxycarbonyl) difluoroanilines: Regiocontol by fluorine in the synthesis of 4-Methoxycarbonyl derivatives*, Synthesis., 1990, pp. 295-299, XP002387592.
Shelley Darnbrough et al., "An Improved Synthesis of N-BOC Protected Aryl Amines," *Synthetic Communications*, vol. 31, No. 21, pp. 3273 to 3280 (2001).
Dale D. Dixon et al., "Synthesis of N-Tert.-Butyl Aromatic Amines Via Heterogeneous Acid Catalysis," *Applied Catalysis*, vol. 62, No. 2, pp. 161-169 (1990).

* cited by examiner

*Primary Examiner*—Taylor Victor Oh
(74) *Attorney, Agent, or Firm*—Wenderoth, Lind & Ponack, L.L.P.

(57) ABSTRACT

The present invention relates to a compound of formula (1), wherein $R^1$, $R^2$, $R^3$, n, and X are as defined in the specification, and a process for producing the same. This compound is useful as an intermediate for the synthesis of compounds useful as pharmaceuticals or agricultural chemicals.

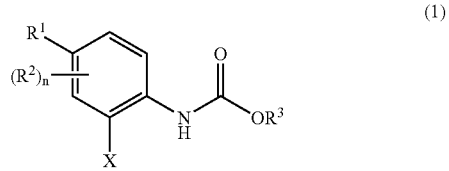

14 Claims, No Drawings

4-ALKYL-2-HALOANILINE DERIVATIVES AND PROCESS FOR PRODUCING THE SAME

BACKGROUND OF THE INVENTION

1. Field of the Invention

The present invention relates to 4-alkyl-2-haloaniline derivatives and a process for producing the same. The 4-alkyl-2-haloaniline derivatives are intermediates for the synthesis of compounds useful as pharmaceuticals or agricultural chemicals.

2. Related Art

It is known that a Friedel-Crafts alkylation reaction of an aniline derivative does not proceed without difficulty. The reason for this difficulty is as follows. In general, in the Friedel-Crafts alkylation reaction of an aniline derivative, a protonic acid or a Lewis acid is used as a catalyst. This catalyst, together with an amino group in the aniline derivative, forms a salt or coordinate bond to lower electron density on the aromatic ring, resulting in lowered reaction rate. In particular, it is known that, in the alkylation of a 2-haloaniline derivative, an electron withdrawing substituent effect of a halogen atom in an ortho position on the aromatic ring relative to the amino group makes it very difficult for the alkylation reaction to proceed.

In order to solve the above problem, two methods have been proposed.

In one of the two methods, the amino group in the 2-haloaniline derivative is first protected with a protective group, such as acetyl, to lower the capability of the amino group that the amino group combines with the protonic acid or the Lewis acid to form a salt or complex bond. Thereafter, the Friedel-Crafts alkylation of the protected 2-haloaniline derivative is carried out. So far as the present inventors know, however, there is no report about successful preparation of a product in which the regioselectivity has been significantly enhanced by this method.

The other method is disclosed in Japanese Patent Laid-Open Publication No. 944/1983. In this method, a 2-haloaniline derivative is alkylated in a closed vessel at a high temperature of 175 to 250° C. under a pressure of 5 to 50 atm to selectively prepare a derivative in which an alkyl group has been introduced into the para or ortho position of the 2-haloaniline derivative.

In this method, however, the alkylation should be carried out under acidic conditions and, at the same time, under high temperature and high pressure conditions. For this reason, in carrying out the reaction, a pressure-resistant and acid-resistant closed vessel should be used. This is disadvantageous from the viewpoint of handleability on a commercial scale. Due to the above reaction conditions, substrates usable in this reaction are disadvantageously limited to highly thermally stable compounds. Further, in aromatic ring coupling reactions such as Still coupling and Suzuki coupling, which have recently drawn attractive attention, aromatic iodine compounds having low thermal stability are generally used. Therefore, the method described in Japanese Patent Laid-Open Publication No. 944/1983, which requires high temperature conditions, cannot be applied to such iodine compounds without difficulties.

Accordingly, a method for synthesizing an alkylation product under mild reaction conditions without the necessity of adopting severe reaction conditions has been desired.

On the other hand, for example, WO 01/92231 discloses 6-t-butyl-8-fluoroquinoline derivatives as a group of compounds having excellent control activity against rice blast. Thus, 4-alkyl-2-haloaniline derivatives can be used as intermediates for the synthesis of pharmaceuticals or agricultural chemicals. When a 4-alkyl-2-haloaniline derivative is synthesized for use in the above applications, the 4-alkyl-2-haloaniline derivative is preferably prepared by an alkylation reaction with high regioselectivity from the viewpoints of the quality and productivity of the final product.

SUMMARY OF THE INVENTION

The present inventors have now found that a 2-haloaniline derivative can be alkylated under milder reaction conditions than the prior art method by previously protecting an amino group, directly attached to the aromatic ring of a 2-haloaniline derivative, with a carbamate-type protective group, such as an alkyloxycarbonyl group, and then carrying out a Friedel-Crafts alkylation reaction. The present inventors have further found that, in this case, the alkylation reaction can be allowed to proceed with high regioselectivity, that is, the 4-position of the aromatic ring in the 2-haloaniline derivative can be alkylated with high selectivity. Further, when this reaction is utilized, a 6-t-butyl-8-fluoroquinoline derivative useful for control of rice blast can be prepared by a synthesis process using the 4-alkyl-2-haloaniline derivative as an intermediate for the synthesis of the 6-t-butyl-8-fluoroquinoline derivative. The present invention has been made based on such finding.

Accordingly, an object of the present invention is to provide a production process of a 4-alkyl-2-haloaniline derivative through the alkylation of a 2-haloaniline derivative, which, as compared with the prior art method, can be carried out under milder reaction conditions and, at the same time, can realize higher regioselectivity with respect to the alkylation of the para position relative to amino in the 2-haloaniline derivative.

Another object of the present invention is to provide a 4-alkyl-2-haloaniline derivative which is useful as an intermediate for the synthesis of compounds useful as pharmaceuticals or agricultural chemicals.

According to one aspect of the present invention, there is provided a compound of formula (1):

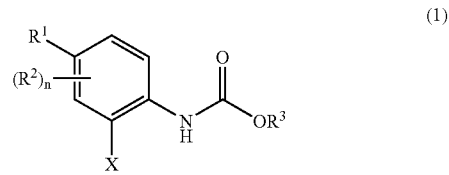

(1)

wherein $R^1$ represents branched chain C3-C10 alkyl or optionally substituted C3-C10 cycloalkyl;

$R^2$ represents a halogen atom, optionally substituted straight chain or branched chain C1-C8 alkyl, or optionally substituted C3-C8 cycloalkyl;

$R^3$ represents optionally substituted straight chain or branched chain C1-C8 alkyl, optionally substituted straight chain or branched chain C2-C6 alkenyl, or optionally substituted C3-C8 cycloalkyl;

n is an integer of 0 (zero) to 3; and

X represents a halogen atom.

According to another aspect of the present invention, there is provided a process for producing the compound of formula (1), comprising the steps of:

providing a 2-haloaniline derivative of formula (2); and reacting the 2-haloaniline derivative with an alkylating agent in the presence of an acid catalyst in an organic solvent or sulfuric acid to introduce group $R^1$, which is as defined in formula (1), into the 4-position of the derivative, thereby preparing the compound of formula (1):

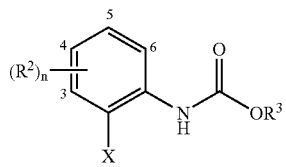

(2)

wherein
$R^2$, $R^3$, n, and X are as defined in formula (1), provided that $R^2$ is not in the 4-position on the aromatic ring.

The use of the compound according to the present invention as an intermediate can realize with high efficiency the synthesis of 6-t-butyl-8-fluoroquinoline derivatives, which are useful as pharmaceuticals or such agricultural chemicals as rice blast control agents. Further, according to the production process of the present invention, the para (4) position relative to amino on the aromatic ring of the 2-haloaniline derivative can be alkylated with high regioselectivity. As a result, a 4-alkyl-2-haloalkyloxycarbonylaniline derivative is obtained, and a 4-alkyl-2-haloaniline derivative, which is generally difficult to produce, can be relatively easily produced with high efficiency by deprotecting the 4-alkyl-2-haloalkyloxycarbonylaniline derivative. By virtue of this high regioselectivity, the production of undesired by-products can be reduced, and the operation efficiency of the whole process can be improved. Further, the process of the present invention can be carried out on a commercial scale thereby. Therefore, the alkylation of the 2-haloaniline derivative can be carried out on a commercial scale. Furthermore, the production process of the present invention can be carried out under mild reaction conditions and thus can also be applied to the alkylation of compounds having low thermal stability such as 2-iodoaniline derivatives.

DETAILED DESCRIPTION OF THE INVENTION

Compounds of Formula (1)

The term "alkyl" as used herein as a group or a part of a group means straight chain, branched chain, or cyclic alkyl unless otherwise specified. Further, for example, "C1-C8" in "C1-C8 alkyl" means that the alkyl group has 1 to 8 carbon atoms.

"Branched chain C3-C8 alkyl" is preferably branched chain C3-C5 alkyl.

Examples of "branched chain C3-C8 alkyl" include isopropyl, i-butyl, t-butyl, t-amyl, and i-hexyl.

"C1-C8 alkyl" is preferably C1-C4 alkyl, more preferably C1-C3 alkyl, still more preferably C1-C2 alkyl.

Examples of "straight chain or branched chain C1-C8 alkyl" include methyl, ethyl, n-propyl, isopropyl, n-butyl, i-butyl, t-butyl, t-amyl, n-pentyl, n-hexyl, n-heptyl, and n-octyl.

"C3-C10 cycloalkyl" is preferably C4-C6 cycloalkyl, more preferably C5-C6 cycloalkyl.

Examples of "C3-C10 cycloalkyl" include cyclopropyl, cyclopropylmethyl, cyclobutyl, cyclopentyl, and cyclohexyl.

"C3-C8 cycloalkyl" is preferably C4-C6 cycloalkyl, more preferably C5-C6 cycloalkyl.

Examples of "C3-C8 cycloalkyl" include cyclopropyl, cyclopropylmethyl, cyclobutyl, cyclopentyl, and cyclohexyl.

"C2-C6 alkenyl" is preferably C2-C4 alkenyl, more preferably C2-C3 alkenyl.

Examples of "straight chain or branched chain C2-C6 alkenyl" include vinyl, isopropenyl, and i-butenyl.

The term "halogen atom" (halide) as used herein means a fluorine, chlorine, bromine, or iodine atom.

The expression "optionally substituted" alkyl as used herein means that one or more hydrogen atoms on alkyl may be substituted by one or more substituents which may be the same or different. It will be apparent to a person skilled in the art that the maximum number of substituents may be determined depending upon the number of substitutable hydrogen atoms on alkyl. This is true of alkenyl and cycloalkyl.

The substituent can be selected from the group consisting of a halogen atom, nitro, ester, straight chain or branched chain C1-C4 alkyl, straight chain or branched chain C1-C4 alkoxy, allyl, nitrophenyl, and C1-C4 alkylsulfonyl.

The term "ester" means ester having 1 to 4 carbon atoms, and examples of the ester include acetic esters, propionic esters, butanoic esters, isobutanoic esters, and cyclopropylcarboxylic esters.

"C1-C4 alkoxy" is preferably C1-C3 alkoxy, more preferably C1-C2 alkoxy. Examples of "C1-C4 alkoxy" include methoxy, ethoxy, n-propoxy, i-propoxy, n-butoxy, i-butoxy, s-butoxy, and t-butoxy.

"C1-C4 alkylsulfonyl" is preferably C1-C3 alkylsulfonyl, more preferably C1-C2 alkylsulfonyl. Examples of "C1-C4 alkylsulfonyl" include methylsulfonyl, ethylsulfonyl, n-propylsulfonyl, n-butylsulfonyl, i-butylsulfonyl, and t-butylsulfonyl.

$R^1$ preferably represents branched chain C3-C5 alkyl or optionally substituted C3-C6 cycloalkyl, more preferably isopropyl, t-butyl, t-amyl, or 1-methylcyclohexyl, still more preferably isopropyl, t-butyl, or 1-methylcyclohexyl, most preferably isopropyl or t-butyl.

$R^2$ preferably represents a halogen atom or straight chain or branched chain C1-C4 alkyl, more preferably a halogen atom or methyl, still more preferably a fluorine atom or methyl.

n is preferably an integer of 0 (zero) to 2, more preferably 0 (zero) or 1, still more preferably 0 (zero).

In another preferred embodiment of the present invention, in formula (1), when n is 1, $R^2$ represents a fluorine atom or methyl.

When n is 1, preferably, $R^2$ is in a 3-, 5-, or 6-position relative to amino on the aromatic ring. More preferably, when n is 1 and $R^2$ represents a fluorine atom, $R^2$ is in a 3- or 6-position relative to amino on the aromatic ring. Alternatively, more preferably, when n is 1 and $R^2$ represents alkyl, $R^2$ is in a 3- or 5-position relative to amino on the aromatic ring.

$R^3$ preferably represents optionally substituted straight chain or branched chain C1-C4 alkyl, vinyl, isopropenyl, or optionally substituted C5-C6 cycloalkyl, more preferably methyl, ethyl, n-propyl, 4-nitrobenzyl, 2-methylsulfonylethyl, vinyl, or isopropenyl, still more preferably methyl or ethyl.

X preferably represents a fluorine, chlorine, or bromine atom, more preferably a fluorine or chlorine atom, still more preferably a fluorine atom.

In a preferred embodiment of the present invention, in formula (1), $R^1$ represents isopropyl, t-butyl, or 1-methylcyclohexyl; $R^3$ represents methyl or ethyl; and n is 0 (zero).

In a more preferred embodiment of the present invention, in formula (1), $R^1$ represents isopropyl or t-butyl; $R^3$ represents methyl or ethyl; n is 0 (zero); and X represents a fluorine atom.

In a still more preferred embodiment of the present invention, in formula (1), $R^1$ represents t-butyl; $R^3$ represents methyl or ethyl; n is 0 (zero); and X represents a fluorine atom.

Specific examples of compounds of formula (1) include 2-chloro-4-isopropyl-N-methoxycarbonylaniline, 2-fluoro-4-isopropyl-N-methoxycarbonylaniline, 2-bromo-4-isopropyl-N-methoxycarbonylaniline, 2-iodo-4-isopropyl-N-methoxycarbonylaniline, 2-chloro-4-isopropyl-N-ethoxycarbonylaniline, 2-fluoro-4-isopropyl-N-ethoxycarbonylaniline, 2-bromo-4-isopropyl-N-ethoxycarbonylaniline, 2-iodo-4-isopropyl-N-ethoxycarbonylaniline, 4-t-butyl-2-chloro-N-methoxycarbonylaniline, 4-t-butyl-2-fluoro-N-methoxycarbonylaniline, 2-bromo-4-t-butyl-N-methoxycarbonylaniline, 4-t-butyl-2-iodo-N-methoxycarbonylaniline, 4-t-butyl-2-chloro-N-ethoxycarbonylaniline, 4-t-butyl-2-fluoro-N-ethoxycarbonylaniline, 2-bromo-4-t-butyl-N-ethoxycarbonylaniline, 4-t-butyl-2-iodo-N-ethoxycarbonylaniline, 4-t-amyl-2-chloro-N-methoxycarbonylaniline, 4-t-amyl-2-fluoro-N-methoxycarbonylaniline, 4-t-amyl-2-bromo-N-methoxycarbonylaniline, 4-t-amyl-2-iodo-N-methoxycarbonylaniline, 4-t-amyl-2-chloro-N-ethoxycarbonylaniline, 4-t-amyl-2-fluoro-N-ethoxycarbonylaniline, 4-t-amyl-2-bromo-N-ethoxycarbonylaniline, 4-t-amyl-2-iodo-N-ethoxycarbonylaniline, 4-t-butyl-2,6-difluoro-N-methoxycarbonylaniline, 4-t-butyl-2,3-difluoro-N-methoxycarbonylaniline, 4-t-butyl-2,6-difluoro-N-ethoxycarbonylaniline, 4-t-butyl-2,3-difluoro-N-ethoxycarbonylaniline, 4-t-butyl-2-fluoro-3-methyl-N-methoxycarbonylaniline, 4-t-butyl-2-fluoro-5-methyl-N-methoxycarbonylaniline, 4-t-butyl-2-fluoro-3-methyl-N-ethoxycarbonylaniline, 4-t-butyl-2-fluoro-5-methyl-N-ethoxycarbonylaniline, 2-fluoro-4-(1-methylcyclohexyl)-N-methoxycarbonylaniline, 2-fluoro-4-(1-methylcyclohexyl)-N-ethoxycarbonylaniline, 2-chloro-4-(1-methylcyclohexyl)-N-methoxycarbonylaniline, 2-chloro-4-(1-methylcyclohexyl)-N-ethoxycarbonylaniline, 2-bromo-4-(1-methylcyclohexyl)-N-methoxycarbonylaniline, and 2-bromo-4-(1-methylcyclohexyl)-N-ethoxycarbonylaniline.

Examples of preferred compounds of formula (1) include 2-fluoro-4-(1-methylcyclohexyl)-N-methoxycarbonylaniline, 2-fluoro-4-(1-methylcyclohexyl)-N-ethoxycarbonylaniline, 4-t-butyl-2-fluoro-N-methoxycarbonylaniline, and 4-t-butyl-2-fluoro-N-ethoxycarbonylaniline.

Production of Compounds of Formula (1)

Compounds of formula (1) according to the present invention may be produced, for example, according to scheme 1. Starting compounds or materials necessary for the synthesis of the compounds according to the present invention are commercially available or can be easily produced by a conventional method.

Scheme 1:

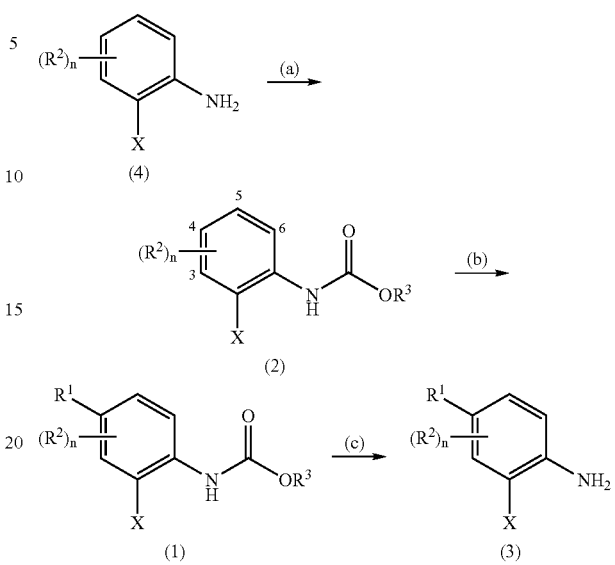

wherein
$R^1$, $R^2$, $R^3$, n, and X are as defined in formula (1)
provided that $R^2$ is not in the 4-position on the aromatic ring in formulae (2) and (4).

Steps in scheme 1 will be described in detail in order.

Step (a):

A 2-haloaniline derivative of formula (2) can be prepared by reacting a compound of formula (4) or its salt with a chloroformic ester $ClCOOR^3$, wherein $R^3$ is as defined in formula (1), under basic conditions to protect amino in the compound of formula (4) or its salt.

Bases usable for providing basic conditions include, for example, pyridine, triethylamine, trimethylamine, morpholine, potassium carbonate, and sodium carbonate.

Specific examples of compounds of formula (4) as the starting compound include: 2-fluoroaniline, 2-chloroaniline, 2-bromoaniline, 2-iodoaniline, 2,6-difluoroaniline, and 2,3-difluoroaniline and salts thereof; 2-fluoro-3-methylaniline; and 2-fluoro-5-methylaniline.

Chloroformic esters usable herein include, for example, alkyl chloroformates, for example, methyl chloroformate, ethyl chloroformate, and alkenyl chloroformates, for example, allyl chloroformate.

The protection reaction of the compound of formula (4) or its salt with the chloroformic ester can be allowed to proceed by causing a substitution reaction in a solvent, such as ethyl acetate, toluene, or tetrahydrofuran, for example, at a temperature of −20° C. to the boiling temperature of the solvent, preferably 0 (zero) to 50° C.

In this reaction, the amino group in the compound of formula (4) is protected with a protective group, for example, alkyloxycarbonyl, alkenyloxycarbonyl, 4-nitrobenzyloxycarbonyl, or 2-methylsulfonylethyloxycarbonyl, to give the 2-haloaniline derivative of formula (2).

Thus, when a carbamate-type protective group such as alkyloxycarbonyl is used, only the para position (4-position)

relative to amino attached to the aromatic ring can be selectively alkylated. When other protective groups, for example, amide-type protective groups such as formyl, acetyl, and pivaloyl, are used, in general, disadvantageously, 5-alkyl compounds, which are compounds substituted at the meta position relative to amino attached to the aromatic ring, are mainly produced due to para orientation domination of 2-substituted halogen.

Specific examples of 2-haloaniline derivatives of formula (2) include 2-fluoro-N-methoxycarbonylaniline, 2-chloro-N-methoxycarbonylaniline, 2-bromo-N-methoxycarbonylaniline, 2-iodo-N-methoxycarbonylaniline, 2-fluoro-N-ethoxycarbonylaniline, 2-chloro-N-ethoxycarbonylaniline, 2-bromo-N-ethoxycarbonylaniline, 2-iodo-N-ethoxycarbonylaniline, 2,6-difluoro-N-methoxycarbonylaniline, 2,3-difluoro-N-methoxycarbonylaniline, 2,6-difluoro-N-ethoxycarbonylaniline, 2,3-difluoro-N-ethoxycarbonylaniline, 2-fluoro-3-methyl-N-methoxycarbonylaniline, and 2-fluoro-5-methyl-N-methoxycarbonylaniline.

Step (b):

Compounds of formula (1) can be produced by introducing various alkyl groups into a 2-haloaniline derivative of formula (2) under conventional Friedel-Crafts alkylation conditions. More specifically, a compound of formula (1) can be produced by reacting a 2-haloaniline derivative of formula (2) with an alkylating agent in the presence of an acid catalyst in an organic solvent or sulfuric acid to introduce group $R^1$, wherein $R^1$ is as defined in formula (1), into the 4-position of the derivative.

The 2-haloaniline derivative of formula (2) may be one produced in step (a), or alternatively may be a commercially available one.

Alkylating agents usable herein include, for example, n-propyl chloride, n-propyl alcohol, isopropyl chloride, isopropyl bromide, isopropyl alcohol, 1-propene, isobutyl chloride, isobutyl bromide, t-butyl alcohol, isobutene, t-butyl chloride, t-butyl bromide, 2-methyl-l-butene, 2-methyl-2-butene, t-amyl alcohol, t-amyl chloride, t-amyl bromide, 1-chloro-2-methylbutane, 1-bromo-2-methylbutane, and 4-propyl-4-heptanol.

In a preferred embodiment of the present invention, the alkylating agent is selected from the group consisting of t-butyl alcohol, isobutene, t-butyl chloride, t-butyl bromide, isobutyl bromide, and isobutyl chloride. More preferably, the alkylating agent is selected from t-butyl alcohol or isobutyl bromide.

For example, when t-butyl is introduced into the derivative of formula (2), the alkylating agent is preferably t-butyl alcohol or isobutyl bromide.

The amount of the alkylating agent used may be properly varied, for example, depending upon the structure and amount of the derivative of formula (2) and the structure of the alkylating agent used. For example, when t-butyl alcohol is used as the alkylating agent, the amount of t-butyl alcohol used is preferably 1.0 to 5.0 moles, more preferably 1.0 to 4.0 moles, based on one mole of the derivative of formula (2).

Preferred acid catalysts include protonic acids and Lewis acids.

A typical example of the protonic acid catalyst is concentrated sulfuric acid. A typical example of the Lewis acid catalyst is anhydrous aluminum chloride. Sulfuric acid which has been diluted with water to a suitable concentration, for example, 50 to 90% sulfuric acid, may also be used as the protonic acid catalyst. Other acid catalysts usable herein include, for example, protonic acids, Lewis acids, or resin catalysts commonly used in conventional Friedel-Crafts reactions, for example, concentrated hydrochloric acid, concentrated nitric acid, stannic chloride, zinc chloride, ferric chloride, and strongly acidic ion exchange resin, Nafion-H resin or other resins.

For example, when t-butyl is introduced into the derivative of formula (2), the use of either a combination of anhydrous aluminum chloride as the acid catalyst with isobutyl bromide as the alkylating agent or a combination of 50 to 90% sulfuric acid as the acid catalyst with t-butyl alcohol as the alkylating agent is preferred. When t-butyl is introduced into the derivative of formula (2), more preferably, a combination of 70 to 80% sulfuric acid as the acid catalyst with t-butyl alcohol as the alkylating agent is used.

Step (b) may be carried out in the absence of a solvent. Preferably, however, step (b) is carried out in a suitable solvent.

When anhydrous aluminum chloride, which is a Lewis acid, is used as the acid catalyst, the solvent is preferably a chlorine-containing solvent such as methylene chloride, chloroform, or tetrachloroethane. In some cases, carbon disulfide or nitrobenzene commonly used in conventional Friedel-Crafts reactions may not be suitable as the solvent.

When concentrated sulfuric acid, which is a protonic acid, is used as the acid catalyst, the concentrated sulfuric acid may also be used as the solvent. In this case, the concentration of the concentrated sulfuric acid is preferably 50 to 90% (w/w), more preferably 70 to 90% (w/w). When concentrated sulfuric acid as such is used, in some cases, large amounts of by-products may be produced, resulting in lowered yield of the target compound.

The amount of the acid catalyst used is preferably 1.5 to 4.0 moles, more preferably 2.0 to 3.0 moles, based on one mole of the derivative of formula (2). This, however, does not apply to the case where a protonic acid such as concentrated sulfuric acid or concentrated hydrochloric acid is used both as the acid catalyst and the solvent.

Step (b) will be described in more details for each acid catalyst type.

When aluminum chloride, which is a Lewis acid, is used as the acid catalyst, step (b) is desirably carried out by providing a mixed solution composed of the derivative of formula (2) dissolved in a solvent, adding aluminum chloride to the mixed solution, heating the mixture at 40 to 60° C. for 30 min to dissolve aluminum chloride in the mixed solution, then cooling the mixed solution to room temperature, adding an alkylating agent thereto, and allowing a reaction to proceed.

In this case, the amount of the alkylating agent used is preferably 1.0 to 6.0 moles, more preferably 4.5 to 5.5 moles, based on one mole of the derivative of formula (2). In the reaction, the alkylating agent may be added to the mixed solution at a time, or alternatively may be introduced in two or more divided portions into the reaction system. Preferably, in the reaction, the alkylating agent is added dropwise to the reaction system over a period of 15 to 30 min.

The optimal reaction temperature varies in the range of a temperature provided under ice cooling to 40° C. depending upon the type of solvent. Therefore, the reaction temperature may be properly varied depending upon the solvent. In general, however, the reaction is preferably carried out at room temperature (for example 20 to 30° C.) from the viewpoint of yield. The reaction time is generally 1 to 4 hr. The disappearance of the evolution of resulting hydrochloric acid gas may be indicative of the completion of the reaction. The resulting hydrochloric acid gas can be efficiently removed from the reaction system by bubbling inert gas, such as nitrogen gas or argon gas, into the reaction system. The bubbling generally can have good effect on yield.

After the completion of the reaction, water or a hydrochloric acid solution is added to the reaction solution to decompose the Lewis acid used as the catalyst, such as aluminum chloride, zinc chloride, or stannic chloride. Subsequently, the reaction solution is extracted with a solvent, which is the same as the reaction solvent, or a nonpolar solvent, such as n-hexane, n-pentane, or ethyl acetate, to give the compound of formula (1) as the target compound. After the removal of the solvent from the extract by distillation, the compound thus obtained as such may be used in the next reaction. Alternatively, the compound may be purified, for example, by distillation or column chromatography on silica gel.

When concentrated sulfuric acid, which is a protonic acid, is used both as the acid catalyst and the solvent, a method is preferably adopted wherein an alkylating agent is added to a mixed solution composed of the derivative of formula (2) dissolved in concentrated sulfuric acid and a reaction is allowed to proceed.

Preferred alkylating agents include, for example, isopropyl bromide and t-butyl bromide and, further, alcohols such as isopropyl alcohol and t-butyl alcohol. In this case, preferably, the alkylating agent is used in an amount of 1.0 to 5.0 moles, more preferably 2.5 to 4.0 moles, based on one mole of the derivative of formula (2). In the reaction, the alkylating agent may be added to the mixed solution either at a time, or alternatively may be introduced in two or more divided portions into the reaction system. Preferably, in the reaction, the alkylating agent is added in three or more divided portions.

The reaction temperature is generally in the range of 50 to 80° C., preferably in the range of 60 to 80° C. The reaction time is generally 3 to 6 hr, preferably 4 to 5 hr.

After the completion of the reaction, the reaction solution is extracted with a solvent such as n-hexane, n-pentane, or a ethyl acetate-n-hexane mixed solution to give the compound of formula (1) as the target compound. After the removal of the solvent from the extract by distillation, the compound thus obtained as such may be used in the next reaction. Alternatively, the compound may be purified, for example, by distillation or column chromatography on silica gel.

Step (c):

The protected amino in the compound of formula (1) is deprotected under acidic or basic conditions to give an aniline derivative of formula (3) or a pharmaceutically acceptable salt or solvate thereof. The deprotection reaction can be carried out by a person having ordinary skill in the art by a conventional method properly selected depending upon the type of the protective group.

For example, when the protective group is alkyloxycarbonyl, substantially quantitative deprotection can be achieved by dissolving the compound of formula (1) in a water-soluble polar solvent, such as methanol or ethanol, adding a 5 to 53% aqueous sodium hydroxide solution or a 5 to 47% aqueous potassium hydroxide solution, and heating the mixture with stirring. The concentration of the aqueous potassium hydroxide solution or the aqueous sodium hydroxide solution is preferably about 30% from the view point of stirring operation. This reaction may also be carried out in the absence of the above solvent. In this case, a 5 to 53%, preferably 20 to 53%, particularly preferably about 30%, aqueous sodium hydroxide solution, or a 5 to 47%, preferably 20 to 47%, particularly preferably about 30%, aqueous potassium hydroxide solution may be used. As described above, for both the aqueous sodium hydroxide solution and the aqueous potassium hydroxide solution, the concentration is preferably about 30% from the viewpoint of stirring operation. Further, in this case, even under conditions other than the above basic conditions, for example, catalytic hydrogenation conditions using palladium or platinum oxide, the compound of formula (1) can be quantitatively deprotected.

Accordingly, in a preferred embodiment of the present invention, there is provided a process for producing an aniline derivative of formula (3) or a pharmaceutically acceptable salt or solvate thereof, said process comprising the steps of: adding, for example, a 20 to 53% aqueous sodium hydroxide solution or a 20 to 47% aqueous potassium hydroxide solution to the compound of formula (1) in the presence of an organic solvent, such as methanol or ethanol, or in the absence of any solvent; and heat treating the mixture optionally under suitable deprotection conditions.

When the protective group is alkenyloxycarbonyl, the compound of formula (1) can be substantially quantitatively deprotected by carrying out the heat treatment in a 47% hydrobromic acid-acetic acid solution.

Specific examples of aniline derivatives of formula (3) produced in step (c) include: 2-fluoro-4-isopropylaniline, 2-chloro-4-isopropylaniline, 2-bromo-4-isopropylaniline, 2-iodo-4-isopropylaniline, 4-t-butyl-2-fluoroaniline, 4-t-butyl-2-chloroaniline, 2-bromo-4-t-butylaniline, 4-t-butyl-2-iodoaniline, 4-t-amyl-2-fluoroaniline, 4-t-amyl-2-chloroaniline, 4-t-amyl-2-bromoaniline, 4-t-amyl-2-iodoaniline, 4-t-butyl-2,6-difluoroaniline, 4-t-butyl-2,3-difluoroaniline, 4-t-butyl-2-fluoro-3-methylaniline, and 4-t-butyl-2-fluoro-5-methylaniline.

The compounds according to the present invention may form pharmaceutically acceptable salts thereof. Preferred examples of such salts include: hydrohalogenide salts such as hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, or maleic acid salts; and amino acid salts such as glutamic acid salts or aspartic acid salts.

Further, in the present invention, the compounds may form solvates, and examples thereof include hydrates, alcoholates, for example, methanolates or ethanolates, and etherates, for example, diethyl etherates.

Applications of Compounds of Formula (1)

The compounds of formula (1) according to the present invention are intermediates for the synthesis of compounds useful as pharmaceuticals or agricultural chemicals.

6-t-Butyl-8-fluoroquinoline derivatives having excellent control activity against rice blast can be easily produced from the compound of formula (1) according to the present invention or the derivative of formula (3) produced from the compound of formula (1) by the synthesis method described in WO 01/92231 or the method described in J. Chem. Soc., (C). 2426 (1970) or Tetrahedron Lett., 4945 (1968). That the 6-t-butyl-8-fluoroquinoline derivatives thus obtained are a group of compounds having excellent control activity against rice blast is as disclosed in WO 01/92231.

For example, 6-t-butyl-2,3-dimethyl-8-fluoroquinolone can be produced by dehydrocondensing 4-t-butyl-2-fluoroaniline produced by the present invention or its salt with ethyl 2-methylacetoacetate by the synthesis method described in WO 01/92231 or the method described in J. Chem. Soc., (C). 2426 (1970) or Tetrahedron Lett., 4945 (1968) to give a Schiff base compound and heating the Schiff base compound in phenyl ether at 250° C. to cyclize the compound into a quinolone ring. 4-Acetoxy-6-t-butyl-2,3-dimethyl-8-fluoroquinoline can be produced by converting this quinolone compound under acetic anhydride-base conditions to 4-o-acetylquinoline. As described in WO 01/92231, this compound has excellent control activity against rice blast.

A synthesis process of 6-t-butyl-8-fluoroquinoline derivative (hereinafter often referred to as "compound of formula (i)") described in WO 01/92231, wherein the derivative of formula (3) produced according to the present invention (particularly 4-t-butyl-2-fluoroaniline) is used as the starting compound, will be specifically described.

The compound of formula (i) can be produced, for example, according to scheme 2 from 4-t-butyl-2-fluoroaniline synthesizable by a known method.

Scheme 2:

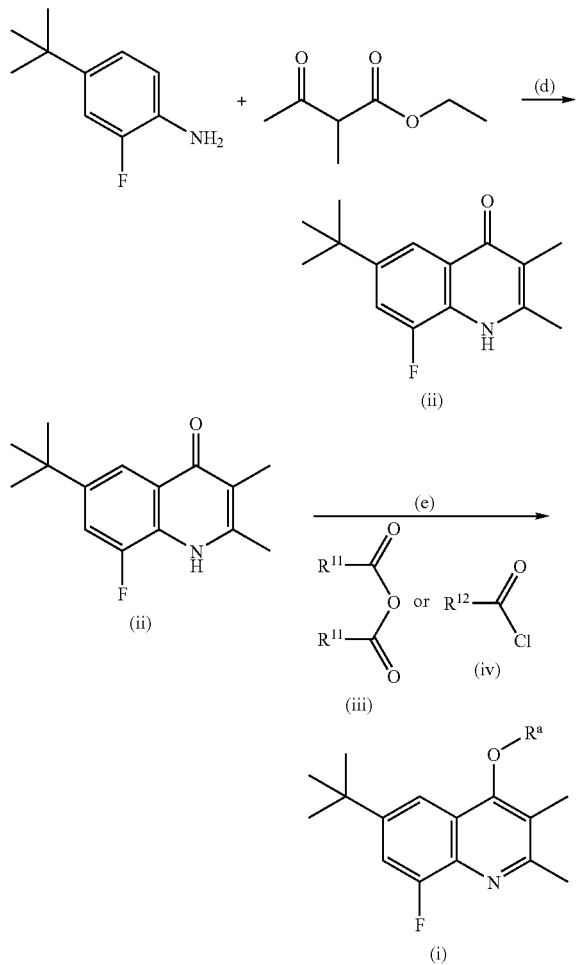

wherein
$R^a$ represents a hydrogen atom, —COR$^{11}$, —COOR$^{11}$, —COCH$_2$OCH$_3$, or —COCH$_2$OCOCH$_3$;
$R^{11}$ represents alkyl having 1 to 4 carbon atoms; and
$R^{12}$ represents —R$^{11}$, —OR$^{11}$, —CH$_2$OCH$_3$, or —CH$_2$OCOCH$_3$.

In this scheme 2, a compound of formula (ii) is first provided (step (d)). Next, if necessary, the compound of formula (ii) is reacted with the compound of formula (iii) or (iv) in the presence or absence of a base (step (e)) to give the compound of formula (i).

Scheme 2 will be described in more detail.

Step (d):
A compound of formula (ii) is first produced from 4-t-butyl-2-fluoroaniline and ethyl 2-methylacetoacetate, for example, according to the method described in J. Am. Chem. Soc. 70, 2402 (1948) or Tetrahedron Lett. 27, 5323 (1986). The compound of formula (ii) corresponds to the compound of formula (i) wherein $R^a$ represents a hydrogen atom. 4-t-Butyl-2-fluoroaniline used can be produced by a conventional method described, for example, in Chem. Abs. 42, 2239 or J. Chem. Soc., Chem. Commun., 1992, 595.

Step (e):
Next, when a compound of formula (i), wherein $R^a$ represents a group other than a hydrogen atom, is desired, the compound of formula (i) can be produced by reacting the compound of formula (ii) with a compound of formula (iii) or (iv) in the presence or absence of a base.

Bases usable herein include, for example, organic amines, such as triethylamine and pyridine, and inorganic bases such as sodium carbonate, potassium carbonate, and sodium hydride. The compound of formula (iii) or (iv) is preferably used in an amount of 1 to 50 equivalents, more preferably 1 to 10 equivalents, based on the compound of formula (ii). The reaction in step (e) can be carried out in an organic solvent in the absence of a solvent or in an organic solvent inert to the reaction, for example, dimethylformamide or tetrahydrofuran, for example, at a temperature in the range of 0 (zero) to 140° C.

EXAMPLES

The following examples further illustrate the present invention, but are not intended to limit it.

Example 1

1-a) Synthesis of 2-fluoro-N-methoxycarbonylaniline

2-Fluoroaniline (10.0 mL, 0.104 mol) was dissolved in ethyl acetate (40 mL) to prepare a solution. Pyridine (10.0 mL, 0.124 mol) was added to the solution, and the mixture was cooled under ice cooling. A solution of methyl chloroformate (8.80 mL, 0.114 mol) in 10 mL of ethyl acetate was added dropwise to the cooled mixture over a period of 30 min. The reaction solution was warmed to room temperature followed by stirring for 3 hr. The disappearance of 2-fluoroaniline from the reaction solution was confirmed by high performance liquid chromatography. Thereafter, 20 mL of water was added thereto under ice cooling to stop the reaction. Next, 50 mL of ethyl acetate and 50 mL of water were added to the reaction mixture to carry out extraction. The organic layer was washed with 40 mL of water and 30 mL of a saturated sodium hydrogencarbonate solution and was then dried over an hydrous magnesium sulfate. The solvent was then removed from the organic layer by distillation to give 16.5 g of 2-fluoro-N-methoxycarbonylaniline as a substantially single product (yield 94.4%).

EI-MS: m/z 170 (M+H)$^+$; $^1$H NMR (CDCl$_3$) δ 3.80 (3H, s, CH$_3$), 6.86 (1H, bs, NH), 6.97-7.09 (2H, m, H$_4$ and H$_5$), 7.12 (1H, t-like, J=7.3 Hz, H$_3$), 8.08 (1H, bs, H$_6$).

1-b) Synthesis of 4-t-butyl-2-fluoro-N-methoxycarbonylaniline using isobutyl bromide 2-Fluoro-N-methoxycarbonylaniline (500 mg, 3.11 mmol) was dissolved in methylene chloride (20 mL) to prepare a solution. Anhydrous aluminum chloride (986 mg, 7.77 mmol) was added to the solution, and the mixture was stirred at 40° C. for 20 min. Thereafter, the reaction solution was cooled to room temperature. A solution of isobutyl bromide (1.60 mL, 15.5 mmol) in a methylene chloride solution (6 mL) was added dropwise to the cooled reaction mixture while bubbling argon gas over a period of 10 min. The mixture was stirred for one hr. Water was added thereto, followed by separation of an organic layer. The organic layer was washed with water and was dried over anhydrous magnesium sulfate. The solvent was then removed from the dried organic layer by distillation to give 779 mg of 4-t-butyl-2-fluoro-N-methoxycarbonylaniline as a crude product. The crude product was further subjected to separation and purification by column chromatography on silica gel to give 433 mg of 4-t-butyl-2-fluoro-N-methoxycarbonylaniline (yield 64.0%, 4-t-butyl form: 5-t-butyl form=88:12).

EI-MS:m/z226(M+H)$^+$; $^1$H NMR (CDCl$_3$) δ 1.31 (9H, s, t-Bu), 3.80 (3H, s, CH$_3$), 6.76 (1H, bs, NH), 7.08 (1H, dd, J=13.1, 2.1 Hz, H$_3$), 7.13 (1H, dd, J=8.2, 1.4 Hz, H$_5$), 7.94 (1H, bs, H$_6$).

1-b') Synthesis of 4-t-butyl-2-fluoro-N-methoxycarbonylaniline using sulfuric acid 2-Fluoro-N-methoxycarbonylaniline (150 g, 0.859 mol) was dissolved in 77.6% sulfuric acid (206 g) to prepare a solution. t-Butyl alcohol (72.9 g, 1.07 mol) was added dropwise to the solution under a nitrogen atmosphere over a period of 30 min while stirring and heating the solution at 70° C. After the completion of the dropwise addition, the reaction solution was vigorously stirred at the same temperature for one hr. t-Butyl alcohol (72.9 g, 1.07 mol) was again added dropwise thereto over a period of 30 min. After the completion of the dropwise addition, the reaction solution was vigorously stirred at the same temperature for one hr. t-Butyl alcohol (72.9 g, 1.07 mol) was again added dropwise thereto over a period of 30 min. After the completion of the dropwise addition, the reaction solution was vigorously stirred at the same temperature for one hr. The reaction solution was cooled to room temperature. n-Hexane (530 mL) was then added to the cooled reaction solution to carry out extraction for separation of the mixture into a sulfuric acid layer and an organic layer. n-Hexane (530 mL) was again added to the sulfuric acid layer to carry out extraction for separation of an organic layer. The organic layers thus obtained were combined, and the combined organic layer was washed with water and saturated brine in that order. The solvent was then removed from the organic layer by distillation to give 307 g of 4-t-butyl-2-fluoro-N-methoxycarbonylaniline as an oily crude product (yield on weight basis 159%, purity as determined by gas chromatography 65.1%, 4-t-butyl form 5-t-butyl form=100:0).

FAB-MS: m/z 226 (M+H)$^+$; $^1$H NMR (CDCl$_3$) δ 3.75 (3H, s), 7.05 (3H, m), 8.05 (1H, m).

1-c) Synthesis of 4-t-butyl-2-fluoroaniline

To 303 g of 4-t-butyl-2-fluoro-N-methoxycarbonylaniline as the crude product was added 657 g of a 30% aqueous sodium hydroxide solution. The mixture was heated under reflux at a temperature around 90° C. for 4 hr and was allowed to cool. Water (1,000 mL) was then added thereto, and the mixture was extracted four times with 500 mL of hexane. The organic layers thus obtained were combined, and 2 M hydrochloric acid was added thereto, followed by vigorous stirring to convert the amino group to a hydrochloride form. Subsequently, an aqueous layer was separated and was adjusted to pH 9 by the addition of aqueous sodium hydroxide solution to bring the amino group to a free form. Extraction was carried out twice with 1,000 mL of toluene. The organic layers thus obtained were combined, and the combined organic layer was washed with saturated brine. The solvent was then removed from the organic layer by distillation to give 92.9 g of 4-t-butyl-2-fluoroaniline as an oily substantially single product (yield 65.6% (yield in two steps of t-butylation-deprotection)).

EI-MS: m/z 170 (M+H)$^+$; $^1$H NMR (CDCl$_3$) δ 1.26 (9H, s, t-Bu), 3.56 (br, NH$_2$), 6.74 (1H, t-like, J=9.3 Hz, H$_6$), 6.95 (1H, ddd, J=7.5, 2.1, 0.7 Hz, H$_5$), 7.94 (1H, dd, J=13.4, 1.9 Hz, H$_3$).

Example 2

Synthesis of 4-t-butyl-2-chloro-N-methoxycarbonylaniline

2-Chloro-N-methoxycarbonylaniline (3.00 g, 16.2 mmol) derived from commercially available 2-chloroaniline was dissolved in 77.6% sulfuric acid (24.0 g) to prepare a solution. t-Butyl alcohol (1.7 mL, 17.8 mmol) was added dropwise to the solution under a nitrogen atmosphere over a period of 30 min while stirring and heating the solution at 70° C. After the completion of the dropwise addition, the reaction solution was vigorously stirred at the same temperature for one hr. Thereafter, t-butyl alcohol (1.7 mL, 17.8 mmol) was again added dropwise thereto over a period of 30 min. After the completion of the dropwise addition, the reaction solution was vigorously stirred at the same temperature for one hr. t-Butyl alcohol (1.7 mL, 17.8 mmol) was again added dropwise thereto over a period of 30 min. After the completion of the dropwise addition, the reaction solution was vigorously stirred at the same temperature for one hr. The reaction solution was cooled to room temperature. n-Hexane (12 mL) was then added thereto to carry out extraction for separation of the mixture into a sulfuric acid layer and an organic layer. n-Hexane (12 mL) was again added to the sulfuric acid layer to carry out extraction for separation of an organic layer. The organic layers thus obtained were combined, and the combined organic layer was washed with water, a saturated aqueous sodium hydrogencarbonate solution, and water in that order. The solvent was then removed from the organic layer by distillation under the reduced pressure to give 4.00 g of a light yellow oil. The oil was further subjected to separation and purification by column chromatography on silica gel to give 2.12 g of 4-t-butyl-2-chloro-N-methoxycarbonylaniline as a target compound (yield 49.5%, 4-t-butyl form: 5-t-butyl form=91:9).

EI-MS: m/z 241 (M)$^+$; $^1$H NMR (CDCl$_3$) δ 1.29 (9H, s, t-Bu), 3.80 (3H, s, CH$_3$), 7.05 (1H, bs, NH), 7.28 (1H, dd, J=8.5, 2.1 Hz, H$_5$), 7.34 (1H, d, J=2.2 Hz, H$_3$), 8.03 (1H, bd, J=8.3 Hz, H$_6$).

Example 3

Synthesis of 2-bromo-4-t-butyl-N-methoxycarbonylaniline

2-Bromo-N-methoxycarbonylaniline (3.00 g, 13.0 mmol) derived from commercially available 2-bromoaniline was dissolved in 77.6% sulfuric acid (19.0 g) to prepare a solution. t-Butyl alcohol (1.40 mL, 14.3 mmol) was added dropwise to the solution under a nitrogen atmosphere over a period of 30 min while stirring and heating the solution at 70° C. After the completion of the dropwise addition, the reaction solution was vigorously stirred at the same temperature for one hr. Thereafter, t-butyl alcohol (1.40 mL, 14.3 mmol) was again added dropwise thereto over a period of 30 min. After the completion of the dropwise addition, the reaction solution was vigorously stirred at the same temperature for one hr. t-Butyl alcohol (1.40 mL, 14.3 mmol) was again added dropwise thereto over a period of 30 min. After the completion of the dropwise addition, the reaction solution was vigorously stirred at the same temperature for one hr. The reaction solution was cooled to room temperature. n-Hexane (10 mL) was then added to the cooled reaction solution to carry out extraction for separation of the mixture into a sulfuric acid layer and an organic layer. n-Hexane (10 mL) was again added to the sulfuric acid layer to carry out extraction for separation of an organic layer. The organic layers thus obtained were combined, and the combined organic layer was washed with water, a saturated aqueous sodium hydrogencarbonate solution, and water in that order. The solvent was then removed from the organic layer by distillation under the reduced pressure to give 4.20 g of light yellow oil. The oil was further subjected to separation and purification by column chromatography on silica gel to give 2.08 g of 2-bromo-4-t-butyl-N-methoxycarbonylaniline as a target compound (yield 55.8%, 4-t-butyl form: 5-t-butyl form=92:8).

EI-MS: m/z 285 (M)$^+$; $^1$H NMR (CDCl$_3$) δ 1.29 (9H, s, t-Bu) 3.80 (3H, s, CH$_3$), 7.04 (1H, bs, NH), 7.33 (1H, dd, J=8.7, 2.2 Hz, H$_5$), 7.50 (1H, d, J=2.2 Hz, H$_3$), 8.01 (1H, bd, J=8.0 Hz, H$_6$).

Example 4

Synthesis of 4-t-butyl-2-iodo-N-methoxycarbonylaniline

2-Iodo-N-methoxycarbonylaniline (2.00 g, 7.22 mmol) derived from commercially available 2-iodoaniline was dissolved in 77.6% sulfuric acid (11.0 g) to prepare a solution. t-Butyl alcohol (2.10 mL, 21.7 mmol) was added dropwise to the solution under a nitrogen atmosphere over a period of 10 min while stirring and heating the solution at 60° C. After the completion of the dropwise addition, the reaction solution was vigorously stirred at the same temperature for 30 min. The reaction solution was cooled to room temperature. n-Hexane (20 mL) was then added to the cooled reaction solution to carry out extraction for separation of the mixture into a sulfuric acid layer and an organic layer. n-Hexane (20 mL) was again added to the sulfuric acid layer to carry out extraction for separation of an organic layer. The organic layers thus obtained were combined, and the combined organic layer was washed with water, a saturated aqueous sodium hydrogencarbonate solution, and water in that order. The solvent was then removed from the organic layer by distillation under the reduced pressure to give 1.36 g of a light brown oil. The oil was further subjected to separation and purification by column chromatography on silica gel to give 0.790 g of 4-t-butyl-2-iodo-N-methoxycarbonylaniline as a target compound (yield 32.8%, 4-t-butyl form: 5-t-butyl form=94:6).

EI-MS: m/z 333 (M)$^+$; $^1$H NMR (CDCl$_3$) δ 1.29 (9H, s, t-Bu), 3.80 (3H, s, CH$_3$), 6.87 (1H, bs, NH), 7.36 (1H, dd, J=8.2, 2.2 Hz, H$_5$), 7.73 (1H, d, J=2.2 Hz, H$_3$), 7.90 (1H, bd, J=8.8 Hz, H$_6$).

Example 5

Synthesis of 2-fluoro-4-isopropyl-N-methoxycarbonylaniline

2-Fluoro-N-methoxycarbonylaniline (1.00 g, 5.92 mmol) prepared as described in Example 1 was dissolved in 77.6% sulfuric acid (5.00 g) to prepare a solution. Isopropyl alcohol (0.400 g, 6.51 mmol) was added to the solution under a nitrogen atmosphere while stirring and heating the solution at 70° C. The mixture was vigorously stirred for 3 hr. The reaction solution was cooled to room temperature. n-Hexane (10 mL) was then added to the cooled reaction solution to carry out extraction for separation of the mixture into a sulfuric acid layer and an organic layer, and this extraction was carried out once again. The organic layers thus obtained were combined, and the combined organic layer was washed with a saturated aqueous sodium hydrogencarbonate solution and saturated brine in that order. The solvent was then removed from the organic layer by distillation to give 666 mg of 2-fluoro-4-isopropyl-N-methoxycarbonylaniline as an oil. The oil was further subjected to separation and purification by column chromatography on silica gel to give 206 mg of 2-fluoro-4-isopropyl-N-methoxycarbonylaniline (yield 17.0%).

EI-MS: m/z 212 (M+H)$^+$; $^1$H NMR (CDCl$_3$) δ 1.22 (6H, d, J=6.8 Hz, isopropyl-Me), 2.88 (1H, m, isopropyl-CH), 3.80 (3H, s, CH$_3$), 6.75 (1H, bs, NH), 6.93 (1H, dd, J=12.9, 2.4 Hz, H$_3$), 6.99 (1H, dd, J=7.8, 2.4 Hz, H$_5$), 7.95 (1H, bs, H$_6$).

Example 6

Synthesis of 2-fluoro-4-(1-methylcyclohexyl)-N-methoxycarbonylaniline

2-Fluoro-N-methoxycarbonylaniline (3.38 g, 20.0 mmol) prepared as described in Example 1 was dissolved in 77.6% sulfuric acid (20 g) to prepare a solution. 1-Methylcyclohexyl alcohol (2.28 g, 20.0 mol) was added dropwise to the solution under a nitrogen atmosphere over a period of 30 min while stirring and heating the solution at 70° C. After the completion of the dropwise addition, the reaction solution was vigorously stirred at the same temperature for 5 hr. Subsequently, the reaction solution was cooled to room temperature. n-Hexane (100 mL) was then added to the cooled reaction solution to carry out extraction for separation of the mixture into a sulfuric acid layer and an organic layer. n-Hexane (100 mL) was again added to the sulfuric acid layer to carry out extraction for separation of an organic layer. The organic layers thus obtained were combined, and the combined organic layer was washed with water and saturated brine in that order. The solvent was then removed from the organic layer by distillation to give 2-fluoro-4-(1-methylcyclohexyl)-N-methoxycarbonylaniline as an oil. The oil was further subjected to separation and purification by column chromatography on silica gel to give 843 mg of 2-fluoro-4-(1-methylcyclohexyl)-N-ethoxycarbonylaniline as a target compound (yield 15.8%, 4-substituted compound: 5-substituted compound=100:0).

EI-MS: m/z 265 (M+H)$^+$; $^1$H NMR (CDCl$_3$) δ 1.15 (3H, s, 1-methyl), 1.42 (4H, m, cyclohexyl), 1.54 (4H, m, cyclohexyl), 1.93 (2H, m, cyclohexyl), 3.80 (3H, s, OCH$_3$), 6.76 (1H, bs, NH), 7.07 (1H, dd, J=13.4, 2.2 Hz, H$_3$-aromatic), 7.12 (1H, dd, J=8.1, 2.0 Hz, H$_5$-aromatic), 7.95 (1H, bs, H$_6$-aromatic).

Example 7

Synthesis of 4-t-butyl-2-fluoro-N-ethoxycarbonylaniline

2-Fluoro-N-ethoxycarbonylaniline (1.00 g, 5.46 mmol) prepared as described in Example 1 was dissolved in 77.6% sulfuric acid (5.00 g) to prepare a solution. t-Butyl alcohol (0.440 g, 6.01 mmol) was added dropwise to the solution under a nitrogen atmosphere over a period of 30 min while stirring and heating the solution at 70° C. After the completion of the dropwise addition, the reaction solution was vigorously stirred at the same temperature for one hr. Thereafter, t-butyl alcohol (0.440 g, 6.01 mmol) was again added dropwise thereto over a period of 30 min. After the completion of the dropwise addition, the reaction solution was vigorously stirred at the same temperature for one hr. t-Butyl alcohol (0.440 g, 6.01 mmol) was again added dropwise thereto over a period of 30 min. After the completion of the dropwise addition, the reaction solution was vigorously stirred at the same temperature for one hr. The reaction solution was cooled to room temperature. n-Hexane (10 mL) was then added to the cooled reaction solution to carry out extraction for separation of the mixture into a sulfuric acid layer and an organic layer. n-Hexane (10 mL) was again added to the sulfuric acid layer to carry out extraction for separation of an organic layer. The organic layers were combined, and the combined organic layer was washed with water and saturated brine in that order. The solvent was then removed from the organic layer by distillation to give 1.45 g of N-ethoxycarbonyl-4-t-butyl-2-fluoroaniline as an oily crude product (yield on weight basis 111%). The crude product was further subjected to separation and purification by column chromatography on silica gel to give 1.17 g of a mixture of 4-t-butyl-2-fluoro-N-ethoxycarbonylaniline with 5-t-butyl-2-fluoro-N-ethoxycarbonylaniline (yield 90%, 4-t-Bu: 5-t-Bu=82:18).

EI-MS:m/z240 (M+H)$^+$; $^1$H NMR (CDCl$_3$) δ 1.28 (9H, s, t-Bu), 1.32 (3H, t, J=7.06 Hz, CH$_3$), 4.24 (2H, q, J=7.06 Hz, CH$_2$), 6.73 (1H, bs, NH), 7.08 (1H, dd, J=13.4, 2.4 Hz, H$_3$), 7.13 (1H, dd, J=8.8, 2.4 Hz, H$_5$), 7.95 (1H, bs, H$_6$).

The invention claimed is:

1. A compound of formula (1):

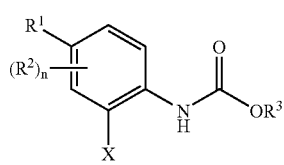

(1)

wherein
R$^1$ represents t-butyl;
R$^2$ represents a halogen atom, straight chain or branched chain C1-C8 alkyl optionally substituted by a halogen atom; nitro, ester having 1 to 4 carbon atoms, C1-C4 alkyl, C1-C4 alkoxy, allyl, nitrophenyl, or C1-C4 alkylsulfonyl; or C3-C8 cycloakly optionally substituted by a halogen atom, nitro, ester having 1 to 4 carbon atoms, C1-C4 alkyl, C1-C4 alkoxy, allyl, nitrophenyl, or C1-C4 alkylsulfony;
R$^3$ represents methyl;
n is zero; and
X represents a fluorine atom.

2. A process for producing the compound of formula (1), comprising the step of reacting the compound of the following formula (2) with an alkylating agent in the presence of an acid catalyst in an organic solvent or sulfuric acid to introduce group R$^1$, into the 4-position of the compound of formula (2), thereby preparing the compound of formula (1):

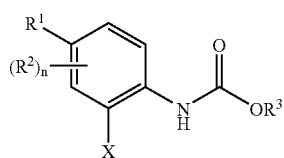

(1)

wherein
R$^1$ represents branched chain C3-C10 alkyl or C3-C10 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;

R$^2$represents a halogen atom, straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;

R3 represents straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; straight chained or branched chain C2-C6 alkenyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;

n is an integer of 0 (zero) to 3; and
X represents a halogen atom,

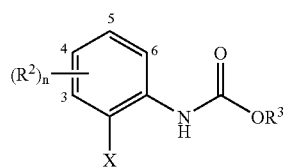

(2)

wherein
R$^2$,R$^3$, n, and X are as defined in the formula (1), provided that R$^2$ is not in the 4-position on the aromatic ring,
wherein the acid catalysts are selected from the group consisting of 50 to 90% sulfuric acid and anhydrous aluminum chloride.

3. The process according to claim 2, wherein the alkylating agent is selected from the group consisting of t-butyl alcohol, isobutene, t-butyl chloride, t-butyl bromide, isobutyl bromide, and isobutyl chloride.

4. The process according to claim 2, wherein said alkylating agent is t-butyl alcohol and said t-butyl alcohol is used in an amount of 1.0 to 5.0 equivalents based on the number of moles of the compound of formula (2).

5. The process according to any one of claims 2 to 4, wherein the acid catalyst is 70 to 90% (w/w) sulfuric acid.

6. The process according to any one of claims 2 to 4, wherein the acid catalyst is 70 to 90% (w/w) sulfuric acid and the reaction is carried out at a temperature in the range of 60 to 80° C.

7. The process according to any one of claims 2 to 4, which further comprises the step of reacting a compound of formula (4) or its salt with a chloroformic ester ClCOOR$^3$, wherein R$^3$ represents straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; straight chain or branched chain C2-C6 alkenyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3 -C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl, under basic conditions to protect amino in the compound of formula (4) or its salt and thus to prepare the compound of formula (2):

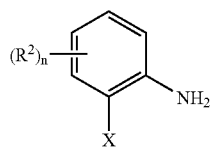

(4)

wherein
- R² represents a halogen atom, straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;
- n is an integer of 0 (zero) to 3; and
- X represents a fluorine or chlorine atom.

8. A process for producing a compound of formula (3) or a pharmaceutically acceptable salt thereof, comprising the step of deprotecting the protected amino in the compound of formula (1) under acidic or basic conditions:

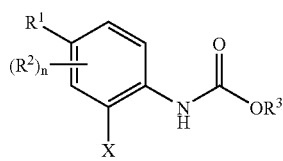

(1)

wherein
- R¹ represents branched chain C3-C10 alkyl or C3-C10 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;
- R² represents a halogen atom, straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;
- R³ represents straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; straight chained or branched chain C2-C6 alkenyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;
- n is an integer of 0 (zero) to 3; and
- X represents a halogen atom,

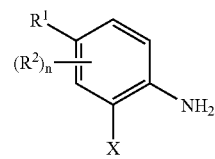

(3)

wherein n, R¹, R², and X are as defined in the formula (1).

9. The compound according to claim 8, wherein R¹ represents t-butyl;
- n is 0; and
- X represents a fluorine atom.

10. The process according to claim 8, wherein the deprotection reaction is carried out by heating the compound of formula (1) in a 20 to 53% aqueous sodium hydroxide solution or a 20 to 47% aqueous potassium hydroxide solution.

11. The process according to any one of claims 8 to 10, which further comprises the step of reacting a compound of formula (2) with an alkylating agent in the presence of an acid catalyst in an organic solvent or sulfuric acid to introduce group R¹, wherein R¹ represents branched chain C3-C10 alkyl or C3 to C10 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; into the 4-position of the compound of formula (2), thereby preparing the compound of formula (1):

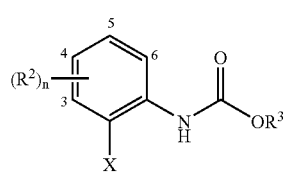

(2)

wherein
- R² represents a halogen atom, straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;
- R³ represents straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; straight chained or branched chain C2-C6 alkenyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;
- n is an integer of 0 (zero) to 3; and
- X represents a fluorine or chlorine atom, provided that R2 is not in the 4-position on the aromatic ring,
- wherein the acid catalysts are selected from the group consisting of 50 to 90% sulfuric acid and anhydrous aluminum chloride.

12. The process according to claim 5, which further comprises the step of reacting a compound of formula (4) or its salt with a chloroformic ester ClCOOR³, wherein R³ represents straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; straight chain or branched chain C2-C6 alkenyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl, under basic conditions to protect amino in the compound of formula (4) or its salt and thus to prepare the compound of formula (2):

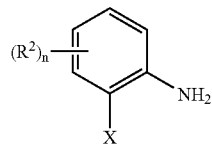

(4)

wherein R², n, and X are as defined in the formula (1).

13. The process according to claim 6, which further comprises the step of reacting a compound of formula (4) or its salt with a chloroformic ester ClCOOR³, wherein R³ represents straight chain or branched chain C1-C8 alkyl optionally substituted by a halogen atom, nitro, ester having 1 to 4 carbon atoms, C1-C4 alkyl, C1-C4 alkoxy, allyl, nitrophenyl, or C1-C4 alkylsulfonyl; straight chain or branched chain C2-C6 alkenyl optionally substituted by a halogen atom, nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl, under basic conditions to protect amino in the compound of formula (4) or its salt and thus to prepare the compound of formula (2):

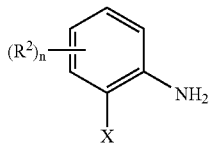

(4)

wherein R², n, and X are as defined in the formula (1).

14. A compound of formula (1):

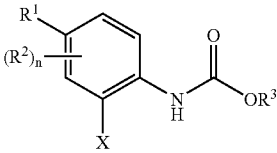

(1)

wherein
R¹ represents t-butyl;
R² represents a halogen atom, straight chain or branched chain C1-C8 alkyl optionally substituted by a halogen atom; nitro, ester having 1 to 4 carbon atoms, C1-C4 alkyl, C1-C4 alkoxy, allyl, nitrophenyl, or C1-C4 alkylsulfonyl; or C3-C8 cycloalkyl optionally substituted by a halogen atom, nitro, ester having 1 to 4 carbon atoms, C1-C4 alkyl, C1-C4 alkoxy, allyl, nitrophenyl, or C1-C4 alkylsulfonyl;
R³ represents ethyl;
n is 0; and
X represents a fluorine atom.

* * * * *